United States Patent
Hansen et al.

(10) Patent No.: US 11,690,814 B2
(45) Date of Patent: Jul. 4, 2023

(54) SUPLATAST TOSILATE FOR USE IN THE TREATMENT OF COUGH ASSOCIATED WITH INTERSTITIAL LUNG DISEASE

(71) Applicant: Conrig Pharma ApS, Copenhagen N (DK)

(72) Inventors: John Bondo Hansen, Copenhagen Ø (DK); Mikael S. Thomsen, Hvidovre (DK); Niels Skjærbæk, Vedbæk (DK)

(73) Assignee: CONRIG PHARMA APS, Copenhagen (DK)

( * ) Notice: Subject to any disclaimer, the term of this patent is extended or adjusted under 35 U.S.C. 154(b) by 163 days.

(21) Appl. No.: 16/061,572

(22) PCT Filed: Nov. 16, 2016

(86) PCT No.: PCT/DK2016/050368
§ 371 (c)(1),
(2) Date: Jun. 12, 2018

(87) PCT Pub. No.: WO2017/108041
PCT Pub. Date: Jun. 29, 2017

(65) Prior Publication Data
US 2019/0254998 A1      Aug. 22, 2019

(51) Int. Cl.
*A61K 31/167*  (2006.01)
*A61P 11/14*   (2006.01)
*A61K 9/00*    (2006.01)

(52) U.S. Cl.
CPC .......... *A61K 31/167* (2013.01); *A61K 9/0073* (2013.01); *A61P 11/14* (2018.01)

(58) Field of Classification Search
CPC .... A61K 31/167; A61K 9/0073; A61K 45/06; A61K 9/0053; A61K 9/2072; A61K 9/2086; A61K 9/209; A61K 9/2866; A61K 9/5084; A61P 11/00; A61P 11/14
USPC ................................................. 514/625, 626
See application file for complete search history.

(56) References Cited

U.S. PATENT DOCUMENTS

| | | | |
|---|---|---|---|
| 4,556,737 A | 12/1985 | Koda et al. | |
| 4,670,583 A | 6/1987 | Koda et al. | |
| 7,897,645 B2 | 3/2011 | Ogawa et al. | |
| 2010/0092562 A1* | 4/2010 | Hollenbeck | A61K 31/00 424/488 |
| 2010/0278915 A1* | 11/2010 | McDermott | A61K 31/4402 424/484 |
| 2016/0354315 A1 | 12/2016 | Li | |

FOREIGN PATENT DOCUMENTS

| | | |
|---|---|---|
| CN | 102210688 A | 10/2011 |
| JP | 2011246454 A | 12/2011 |
| WO | 2011/005352 A1 | 1/2011 |
| WO | 2012159237 A1 | 11/2012 |

OTHER PUBLICATIONS

Miyamoto et al. (Usefulness of suplatast tosilate for chronic cough following lung cancer surgery. Gen Thorac Cardiovasc Surg 57, 463-466 (2009) doi:10.1007/s11748-009-0426-0).*
Kevin K. Brown, MD, FCCP. (Chest 2006; 129:180S-185S).*
Takanobu Shioya European Journal of Clinical Pharmacology 58(3):171-6 • Jul. 2002 DOI: 10.1007/s00228-002-0468-z,Effect of suplatast tosilate, a Th2 cytokine inhibitor, on cough variant asthma).*
Makoto Furonaka et al. (The Journal of Pharmacology and Experimental Therapeutics, Jan. 2009, 328 (1) 55-61; DOI: https://doi.org/10.1124/jpet.108.141721, Suplatast Tosilate Prevents Bleomycin-Induced Pulmonary Fibrosis in Mice).*
Yuji Tohda et al. (Effects of suplatast tosilate (IPD Capsules®) on the production of active oxygen by neutrophils and of IL-8 by mononuclear cells, International Immunopharmacology, vol. 1, Issue 6, Jun. 2001, pp. 1183-1187 https://doi.org/10.1016/S1567-5769(01)00053-4.*
Fukuhara et al., "Suplatast Tosilate Protects the Lung Against Hyperoxic Lung Injury by Scavenging Hydroxyl Radicals", Free Radical Biology and Medicine, vol. 106, 1-9, Year 2017.
Izumi et al., "Suplatast Tosilate Reduces Radiation-Induced Lung Injury in Mice Through Suppression of Oxidative Stress," Free Radical Biology and Medicine, vol. 136, 52-59, Year 2019.
Van Manen et al., Eur. Respir. Rev. 25: 278-286 (2016).
Yang et al., Chin. J. Tuberc. Respir. Dis. 38(12): 928-933 (2015).
Birring et al.: "A novel formulation of inhaled sodium cromoglicate (PA101) in idiopathic pulmonary fibrosis and chronic cough: a randomised, double-blind, proof-of-concept, phase 2 trial". Lancet Respir Med 2017, published online Sep. 8, 2017 http://dx.doi.org/10.1016/S2213-2600(17)30310-7, pp. 1-10.
Brown, Kevin K., MD, FCCP: "Chronic Cough due to Chronic Interstitial Pulmonary Diseases". Chest 129/1, Jan. 2006, pp. 180S-185S.
Cottin et al.: "Fibrosis interstitial lung diseases: knowns and unknowns". Eur Respir Rev 2019; 28:180100, [https://doi.org/10.1183/16000617.0100-2018].
Goos et al.: "Progression in the Management of Non-Idiopathic Pulmonary Fibrosis Interstitial Lung Diseases, Where Are We Now and Where We Would Like to Be". J. Clin. Med. 2021, 10, 1330. https://doi.org/10.3390/jcm10061330.
Guo et al.: "Increased expression of lung TRPV1/TRPA1 in a cough model of bleomycin-induced pulmonary fibrosis in Guinea pigs". BMC Pulmonary Medicine (2019) 19:27. https://doi.org/10.1186/s12890-019-1792-z.
Korsten et al. "Editorial: Interstitial Lung Disease in the Context of Systemic Disease: Pathophysiology, Treatment and Outcomes". Front. Med. 7:644075. https://doi.org/10.3389/fmed.2020.644075.
Liu et al. (Rittie ed.) "The Bleomycin Model of Pulmonary Fibrosis". Fibrosis: Methods and Protocols, Methods in Molecular Biology, vol. 1627, pp. 27-42.
Saito "The Long-term effect of Suplatast Tosilate in the patients with pulmonary fibrosis" Chest 2010; 138 (4_MeetingAbstracts):535A doi:10.1378/chest.9927.

(Continued)

*Primary Examiner* — Savitha M Rao
(74) *Attorney, Agent, or Firm* — Dinsmore & Shohl LLP

(57) ABSTRACT

Provided is a composition comprising suplatast tosilate or pharmaceutically acceptable derivatives thereof for use in a method of treating cough associated with interstitial lung disease, such as cough associated with pulmonary fibrosis.

21 Claims, No Drawings

(56) References Cited

OTHER PUBLICATIONS

Yoshihisa Ishiura et al, Effect of an Orally Active Th2 Cytokine Inhibitor, Suplatast Tosilate, on "Atopic Cough"; Drug Research 2008; 58(6): 297-302.
Luca Richeldi et al, Efficacy and Safety of Nintedanib in Idiopathic Pulmonary Fibrosis; The New England Journal of Medicine, May 29, 2014, vol. 370, No. 22, 2071-2082.
Arata Azuma et al, Exploratory analysis of a phase III trial of pirfenidone identifies a subpopulation of patients with idiopathic pulmonary fibrosis as benefiting from treatment; Respiratory Research 2011, 12:143, 1-11.
Makoto Furonaka et al, Suplatast Tosilate Prevents Bleomycin-Induced Pulmonary Fibrosis in Mice; J Pharmacol Exp Ther. Jan. 2009, 328(1): 55-61.
Jian-Rong Zhou et al, Novel Antitussive Effect of Suplatast Tosilate in Guinea Pigs; Pharmacology, 2015; 95(1-2):36-41.
Yoshihisa Ishiura, Th2 cytokine inhibition and cough in asthmatic and bronchitic patients; Ann Med 2004; 36:623-629.
Joan Antoni Fernandez-Blanco et al, Enhanced cough reflex in a model of bleomycin-induced lung fibrosis in guinea pigs; Clinical Science (2015) 129, 1001-1010.
Won-Serk Kim et al, Accelerated Wound Healing by S-Methylmethionine Sulfonium: Evidence of Dermal Fibroblast Activation via the ERK1/2 Pathway; Pharmacology 2010, 85:68-76.
Karen Methling et al, Investigation of the In Vitro Metabolism of the Analgesic Flupirtine; Drug Metabolism and Disposition, 2009, 37:479-493.
Hideaki Miyamoto et al, Usefulness of suplatast tosilate for chronic cough following lung cancer surgery; Gen Thorac Cardiovasc Surg (2009) 57:463-466.
A.H. Morice et al, ERS guidelines on the assessment of cough; Eur Respir J 2007; 29: 1256-1276.
S. Myou et al, Effects of suplatast tosilate, a new type of anti-allergic agent, on airway cough hypersensitivity induced by airway allergy in guinea-pigs; Clinical and Experimental Allergy, 2001, vol. 31, 1939-1944.
Takanobu Shioya et al, Effect of suplatast tosilate, a Th2 cytokine inhibitor, on cough variant asthma; Eur J Clin Pharmacol (2002) 58:171-176.
Akio Suzuki et al, Identification of Human Cytochrome P-450 Isoforms Involved in Metabolism of R(+)- and S(−)-Gallopamil: Utility of In Vitro Disappearance Rate; Drug Metabolism and Disposition, 1999, vol. 27, No. 11, 1254-1259.
Yukio Tada et al, Synthesis and Antiallergic Activity of Dimethyl-2-(phenylcarbamoyl)ethylsulfonium p-Toluenesulfonate Derivates; J. Med. Chem. 1998, 41, 3330-3336.

* cited by examiner

SUPLATAST TOSILATE FOR USE IN THE TREATMENT OF COUGH ASSOCIATED WITH INTERSTITIAL LUNG DISEASE

TECHNICAL FIELD

The present invention relates to a composition comprising a compound of formula I (suplatast tosilate) or a pharmaceutically acceptable derivative thereof, for use in a method of treating cough associated with interstitial lung disease, such as cough associated with pulmonary fibrosis, such as idiopathic pulmonary fibrosis.

BACKGROUND

Cough is an airway defensive reflex facilitating clearance of accumulated secretions and protecting airways and lungs from aspiration, inhaled particulates and irritants. However, when associated with disease, coughing can be a distressing symptom significantly affecting patient's lifestyle and well-being The marked decrease in health-related quality of life is responsible for cough being the most common symptom bringing patients to medical attention and indeed is one of the primary causes for patients with as yet undiagnosed idiopathic pulmonary fibrosis (IPF) to seek medical assistance.

Cough can be subdivided into acute cough lasting for less than 3 weeks, sub-acute cough lasting between 3 and 8 weeks and chronic cough lasting for more than 8 weeks. Acute cough is most frequently associated with upper respiratory infection and although usually self-limiting, both prescription and over the counter medication are commonly used to treat it with limited success.

Chronic cough is a common symptom of respiratory conditions such as chronic obstructive pulmonary disease (COPD), asthma, upper airways cough syndrome, idiopathic pulmonary fibrosis and some non-respiratory conditions such as gastro oesophageal reflux disease. If the underlying disease is identified and appropriately treated, the cough will often disappear. However, there remains a significant cohort of patients for whom no specific cause of the cough can be identified, and a significant cohort of patients who receives a diagnosis but wherein the underlying disease is currently insufficiently treated at least with respect to reducing the associated cough.

Since persistent cough is often debilitating, embarrassing and significant affects quality of life in severely sick patients, there is a clear need for an effective antitussive agent. Current therapies for the management of cough are of limited benefit to many patients, and involve undesirable side effects or dose-limiting toxicities. Thus, there is still a need for improved therapies for the management and treatment of cough, especially those that have the capacity to reduce cough without having adverse effects.

Suplatast tosilate (ST) is marketed in Japan for oral treatment of atopic dermatitis, asthma and allergy (rhinitis). It is characterized by its ability to inhibit Th2 cytokine production and by its high degree of safety.

ST has been shown in pre-clinical and clinical investigations to have a sub-chronic effect on cough associated with an inflammatory component; namely by i) inhibiting airway cough hypersensitivity underlying allergic eosinophilic inflammation (Myou et al: Clinical and Experimental Allergy, 2001, 31, 1939-1944); ii) improving cough in a capsaicin challenge in patients with Cough Variant Asthma (Shioya et al: Eur J Clin Pharmacol (2002) 58: 171-176); and iii) decreasing cough threshold measured after four weeks of treatment in Atopic cough (Ishiura et al: Arzneimittel-Forschung (Drug Research) 2008; 58(6):297-302).

Also, ST has been shown to reduce citric acid+enalapril induced cough in guinea pigs (Zhou et al: Pharmacology. 2015; 95(1-2): 36-41), and to benefit refractory chronic dry cough following lung cancer surgery (Miyamoto et al: Gen Thorac Cardiovasc Surg. 2009; 57(9): 463-6).

Suplatast tosilate is not effective in all types of cough. It has been found that ST does not change the cough reflex sensitivity in patients with non-atopic asthma or chronic bronchitis (Ishiura et al: Arzneimittel-Forschung (Drug Research) 2008; 58(6):297-302).

Also, while ST was shown to have effect upon sub-chronic administration to reduce airway cough hypersensitivity induced by airway allergy in guinea-pigs, it was determined that ST does not acutely reduce capsaicin induced cough in this model (Miyamoto et al: Gen Thorac Cardiovasc Surg. 2009; 57(9): 463-6).

SUMMARY

The present inventors show herein that suplatast tosilate reduces cough, and in particular reduces cough in a model for interstitial lung disease. Suplatast tosilate thus has potential also for treating cough having non-asthmatic and non-allergic aetiologies, by directly targeting the cough per se, rather than the underlying lung pathology. This provides a potential acute, safe and effective new treatment for cough, including cough associated with interstitial lung disease, such as pulmonary fibrosis-associated cough.

It is an aspect to provide composition comprising a compound of formula (I):

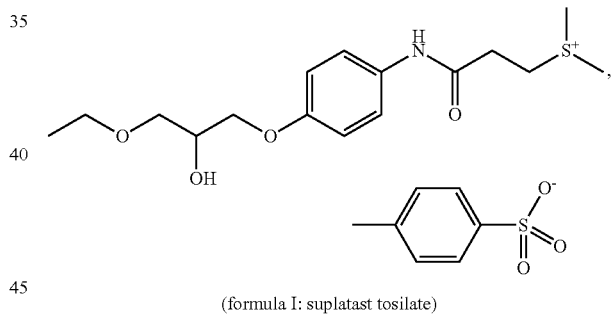

(formula I: suplatast tosilate)

or a pharmaceutically acceptable derivative thereof,
for use in a method of treating cough associated with interstitial lung disease.

In one embodiment said cough is associated with lung fibrosis (pulmonary fibrosis). In one embodiment said cough is associated with idiopathic pulmonary fibrosis (IPF).

In one embodiment said treatment reduces the frequency of cough and/or the severity of cough.

In one embodiment said composition comprises, separately or together, one or more additional active pharmaceutical ingredients, such as additional anti-tussives.

Definitions

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes esters and prodrugs, or other precursors of a compound which may be biologically metabolized into the active compound, or crystal forms of a compound.

The term "acid addition salt" is intended to include "pharmaceutically acceptable acid addition salt" which indicates salts which are not harmful to the patient. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 66, 2, (1977) which is incorporated herein by reference.

The term "therapeutically effective amount" of a compound as used herein refers to an amount sufficient to cure, alleviate, prevent, reduce the risk of, or partially arrest the clinical manifestations of a given disease or disorder and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The terms "treatment" and "treating" as used herein refer to the management and care of a patient for the purpose of combating a condition, disease or disorder. The term is intended to include the full spectrum of treatments for a given condition from which the patient is suffering. The patient to be treated is preferably a mammal, in particular a human being. Treatment of animals, such as mice, rats, dogs, cats, horses, cows, sheep and pigs, is, however, also within the scope of the present context. The patients to be treated can be of various ages.

DETAILED DESCRIPTION

Suplatast tosilate ((±)-3-{[4-(3-ethoxy-2-hydroxypropoxy)phenyl]amino}-3-oxopropyl)(dimethyl)sulfonium; 4-methylbenzenesulfonate) (abbreviated ST herein) is a drug marketed in Japan for oral treatment of atopic dermatitis, asthma and allergy (rhinitis). It is characterized by its ability to inhibit Th2 cytokine production and by its high degree of safety. It is approved for treatment of children and has during its 15 years on the market only been associated with very few serious adverse effects.

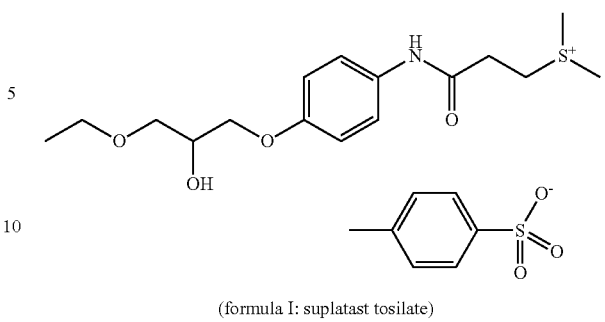

(formula I: suplatast tosilate)

Suplatast tosilate is a racemic mixture. There are no significant differences between the two enantiomers with respect to pharmacology (Tada et al: J. Med. Chem. 1998, 41, 3330-3336).

Suplatast tosilate was developed as a derivative of S-methylmethionine in the attempt to identify sulfonium compounds with immunological activities with the ultimate goal to find a suitable clinical candidate for the treatment of allergic disorders (Tada et al: J. Med. Chem. 1998, 41, 3330-3336). The potential therapeutic effects of S-methylmethionine in cytoprotection and wound healing have been described (Kim et al: Pharmacology 2010; 85: 68-76).

Pathologic cough, particularly if chronic, can become life-altering for patients, affecting overall quality of life, and ability to maintain relationships and jobs. Social isolation and depression often become significant factors for these patients, as pathologic coughers are ostracized in public venues such as the work place, restaurants, public transport, theatre's, etc. Many chronic cough patients cough persistently especially during the active daytime period. Patients with IPF are among those with the most severe cough, the most debilitating symptom of their disease.

Currently available anti-tussive drugs have shown little objective evidence that they are effective for cough in any disorder. Further, safety and abuse liability concerns have restricted use of certain narcotic anti-tussives. The last new cough therapy to be approved was dextromethorphan nearly 50 years ago. To date, no other agent in development has shown effectiveness in the treatment of pathologic cough, especially using objective measures of cough frequency.

Cough is the symptom for which patients most often seek medical attention, and chronic cough due to any cause affects an estimated 5-18% of the general population.

ST has to date been shown to have effect in cough having an underlying aetiology associated with inflammation and allergies, based on a long-term treatment of the underlying allergic disorders that ST is known to target. This potentially provides for a sub-chronic treatment of the underlying cause of the cough, thereby indirectly reducing cough, rather than targeting or treating the cough per se.

It is an aspect to provide a composition comprising a compound of formula (I):

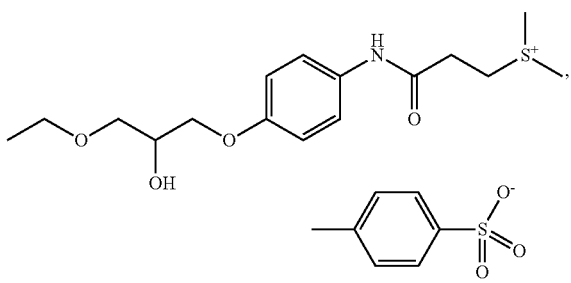

(formula I: suplatast tosilate)

or a pharmaceutically acceptable derivative thereof, for use in a method of treating cough associated with interstitial lung disease.

It is also an aspect to provide use of a composition comprising a compound of formula (I):

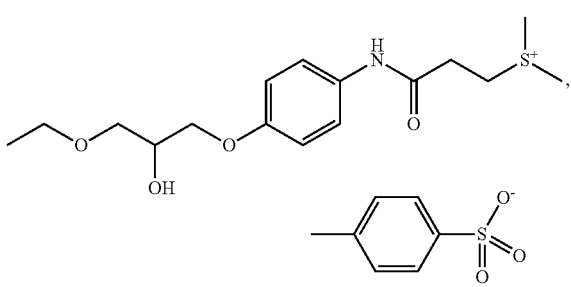

(formula I: suplatast tosilate)

or a pharmaceutically acceptable derivative thereof, for the manufacture of a medicament for the treatment of cough associated with interstitial lung disease.

Also disclosed is a method for treating cough associated with interstitial lung disease comprising administration of a composition comprising a compound of formula (I):

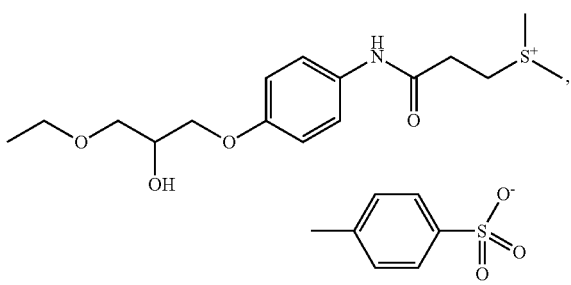

(formula I: suplatast tosilate)

or a pharmaceutically acceptable derivative thereof, to an individual in need thereof.

It is also aspect to provide a composition comprising a compound of formula (I):

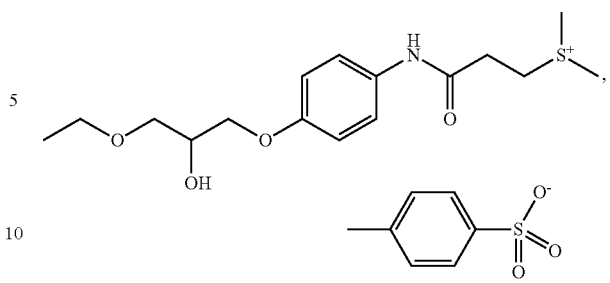

(formula I: suplatast tosilate)

or a pharmaceutically acceptable derivative thereof, for use in a method of treating cough in an individual with interstitial lung disease.

Interstitial lung disease (ILD) is also known as diffuse parenchymal lung disease (DPLD). It is a group of lung diseases affecting the interstitium, which is the tissue and space around the air sacs of the lungs. It involves alveolar epithelium, pulmonary capillary endothelium, basement membrane, perivascular and perilymphatic tissues. All forms of interstitial lung disease cause thickening of the interstitium. The thickening can be due to inflammation, scarring, or extra fluid (edema).

Prolonged ILD may result in pulmonary fibrosis.

Idiopathic pulmonary fibrosis is interstitial lung disease for which no obvious cause can be identified (idiopathic), and is associated with typical radiographic (basal and pleural based fibrosis with honeycombing) and pathologic (temporally and spatially heterogeneous fibrosis, histopathologic honeycombing and fibroblastic foci) findings.

In pathology, honeycomb lung refers to the fibrotic cystic changes (honeycomb changes) seen in the lungs of those with certain end-stage interstitial lung diseases. Honeycomb lung is a pathologic finding and not a specific disease entity. The importance of honeycomb lung is that its presence is associated with a poor prognosis.

Causes of ILD (and thus pulmonary fibrosis) include exogenous agents, inhaled substances, drug-induced, connective tissue disease, infection, malignancies and idiopathic ILD. ILD is not a single disease, but encompasses many different pathological processes. Hence treatment of the underlying pathology is different for each disease.

Many cases due to unknown or connective tissue-based causes are treated with corticosteroids. Some people respond to immunosuppressant treatment. Patients with a low level of oxygen in the blood may be given supplemental oxygen. Recently a new drug for the treatment of Idiopathic Pulmonary Fibrosis (IPF) was approved in the US, Ofev (nintedanib). It has been shown to slow the decline of lung function although the drug has not been shown to reduce mortality or improve lung function.

Reference herein to cough associated with interstitial lung disease is meant to encompass treatment of the cough per se, which cough is associated with induced by, caused by, related to the underlying interstitial lung disease. It is not meant to encompass treatment of the underlying pathology per se which pathology may cause or exacerbate cough, i.e. it is not meant to encompass direct treatment of an interstitial lung disease such as pulmonary fibrosis.

Treatment of cough associated with interstitial lung disease in one embodiment means treatment of cough in an individual or subject with an interstitial lung disease, such as treatment of cough occurring in an individual or subject with an interstitial lung disease, including pulmonary fibrosis.

In one embodiment, cough associated with interstitial lung disease is synonymous with interstitial lung disease-accompanied cough.

In one embodiment said cough associated with interstitial lung disease is pathologic cough associated with interstitial lung disease.

In one embodiment said cough associated with interstitial lung disease is chronic cough associated with interstitial lung disease.

In one embodiment there is provided a composition comprising a compound of formula (I), suplatast tosilate, or a pharmaceutically acceptable derivative thereof, for use in a method of treating chronic cough associated with interstitial lung disease.

In one embodiment there is provided a composition comprising a compound of formula (I), suplatast tosilate, or a pharmaceutically acceptable derivative thereof, for use in a method of acutely treating cough associated with interstitial lung disease.

Acute treatment may be defined as less than sub-chronic treatment. The division between acute, sub-chronic and chronic treatment and effect may differ, and in one embodiment an acute treatment implies an acute effect is observed sooner that with a sub-chronic or chronic treatment. An acute effect may manifest within a few days or a few weeks, such as within one week or within two weeks. An acute effect may require chronic treatment to persist.

In one embodiment there is provided a composition comprising a compound of formula (I), suplatast tosilate, or a pharmaceutically acceptable derivative thereof, for use in a method of treating cough associated with interstitial lung disease, such as pulmonary fibrosis, wherein said interstitial lung disease is:

ILD of known cause or associated with
  Exposure
    Occupation, environment, avocation, medication, drug, radiation, smoking
      inhalation of mineral dusts causing pneumoconiosis, including coal worker's pneumoconiosis (CWP), silicosis, asbestosis, hard metal lung disease, mixed dust pneumoconiosis, graphitosis, berylliosis, and talcosis
      drug-induced: Although the oral and intravenous routes are most commonly associated with pulmonary fibrosis, pulmonary fibrosis can occur with any route of drug delivery. There are many interstitial patterns caused by drugs such as nonspecific interstitial pneumonia (NSIP), usual interstitial pneumonia (UIP), eosinophilic pneumonia, desquamative interstitial pneumonia (DIP), lymphocytic (or lymphoid) interstitial pneumonia (LIP), COP (cryptogenic organizing pneumonia) and granulomatous reactions. The prevalence of drug-induced pulmonary fibrosis is variable and highly dependent on the drug. For example 0.01% of patients receiving nitrofurantoin get pulmonary fibrosis while up to 40% of patients taking amiodarone develop pulmonary fibrosis
  Systemic disease
    CTD (connective tissue disease), IBD (inflammatory bowel disease), sarcoidosis
  Genetic
    Familial ILD, HPS (Hermansky-Pudlak syndrome)
ILD of unknown cause
  IIP (idiopathic interstitial pneumonia)
  IPF (idiopathic pulmonary fibrosis))
  Specific pathology
    LAM (lymphangioleiomyomatosis), PAP (pulmonary alveolar proteinosis.

In one embodiment there is provided a composition comprising a compound of formula (I), suplatast tosilate, or a pharmaceutically acceptable derivative thereof, for use in a method of treating cough associated with interstitial lung disease, wherein said cough associated with interstitial lung disease is selected from the group consisting of:
cough associated with pulmonary fibrosis,
cough associated with idiopathic pulmonary fibrosis (IPF),
cough associated with honeycomb lung caused by ILD such as IPF,
chronic obstructive pulmonary disease (COPD),
cough associated with sarcoidosis,
cough associated with congestive heart disease,
cough associated with pulmonary veno-occlusive disease,
cough associated with pulmonary edema,
cough associated with chronic eosinophilic pneumonia,
cough associated with cryptogenic organizing pneumonia,
cough associated with pulmonary alveolar proteinosis,
cough associated with connective tissue associated interstitial lung diseases,
cough associated with pulmonary fibrosis associated with connective tissue diseases,
cough associated with chronic aspiration,
cough associated with infection-induced lung disease,
cough associated with malignancy-induced lung disease,
cough associated with drug-induced lung disease,
cough associated with inhaled substance-induced lung disease, such as mineral dusts,
cough associated with pneumoconiosis,
cough associated with silicosis,
cough associated with berylliosis,
cough associated with asbestosis,
cough associated with hard metal lung disease,
cough associated with mixed dust pneumoconiosis,
cough associated with graphitosis,
cough associated with talcosis,
cough associated with coal workers pneumoconiosis,
cough associated with carmustine related pulmonary fibrosis,
cough associated with respiratory bronchiolitis,
cough associated with alveolar microlithiasis
cough associated with pulmonary langerhans cell histiocytosis,
cough associated with ground glass opacities,
cough associated with respiratory bronchiolitis associated interstitial lung disease,
cough associated with nonspecific interstitial pneumonia,
cough associated with desquamative interstitial pneumonia,
cough associated with usual interstitial pneumonia,
cough associated with lymphoproliferative disorders,
cough associated with lymphoma,
cough associated with pulmonary lymphangioleiomyomatosis,
cough associated with lymphangitic carcinomatosis,
cough associated with lymphadenopathy, and
cough associated with lymphocytic interstitial pneumonia.

In one embodiment said cough associated with interstitial lung disease is combined pulmonary fibrosis and emphysema.

In one embodiment said cough associated with interstitial lung disease is not associated with (caused or induced by) an inflammatory component.

In one embodiment said cough associated with interstitial lung disease is not associated with (caused or induced by) airway cough hypersensitivity, allergic eosinophilic inflammation, asthma and atopic cough.

In one embodiment there is provided a composition comprising a compound of formula (I), suplatast tosilate, or a pharmaceutically acceptable derivative thereof, for use in a method of treating cough associated with interstitial lung disease, wherein said cough associated with interstitial lung disease is cough associated with pulmonary fibrosis.

In one embodiment there is provided a composition comprising a compound of formula (I), suplatast tosilate, or a pharmaceutically acceptable derivative thereof, for use in a method of treating cough associated with pulmonary fibrosis.

In one embodiment there is provided a composition comprising a compound of formula (I), suplatast tosilate, or a pharmaceutically acceptable derivative thereof, for use in a method of treating cough associated with idiopathic pulmonary fibrosis (IPF).

Improvement

In one embodiment treatment of cough associated with interstitial lung disease means that coughing is reduced.

In one embodiment treatment of cough associated with interstitial lung disease means that the frequency of cough is reduced. This may be evaluated using a frequency score such as the conventional frequency score method. In one embodiment a cough frequency score (0-10) can be obtained using a visual analogue scale: 0=I never cough; 10=I cough all day.

In one embodiment the cough frequency score (0-10) is reduced by approximately 1 point, such as by 2 points, such as by 3 points, such as by 4 points, such as by 5 points, such as by 6 points, such as by 7 points, such as by 8 points, such as by 9 points, such as by 10 points.

In one embodiment the cough frequency score (0-10) is reduced by 0 to 1 points, 1 to 2 points, such as by 2 to 3 points, such as by 3 to 4 points, such as by 4 to 5 points, such as by 5 to 6 points, such as by 6 to 7 points, such as by 7 to 8 points, such as by 8 to 9 points, such as by 9 to 10 points.

Frequency of cough may be measured simply by the number of coughs during a certain observed time period. These may be referred to as objective scores.

In one embodiment frequency of cough is reduced to approximately 90%, such as 80%, such as 70%, such as 60%, such as 50%, such as 40%, such as 30%, such as 20%, such as 10% of the observed frequency without treatment or prior to treatment.

In one embodiment frequency of cough is reduced to approximately 10 to 20%, such as 20 to 30%, such as 30 to 40%, such as 40 to 50%, such as 50 to 60%, such as 60 to 70%, such as 70 to 80%, such as 80 to 90% of the observed frequency without treatment or prior to treatment.

In one embodiment the antitussive effect or percentage inhibition of the number of cough is from 20 to 100%, such as 20%, 30%, 40%, 50%, 60%, 70%, 80%, 90% or up to 100% percentage inhibition. In one embodiment the antitussive effect of suplatast tosilate is 30 to 90%, such as 40 to 80%, such as 50% or more. In one embodiment the antitussive effect of suplatast tosilate is 30 to 90%, such as 40 to 80%, such as 40% or 50% or more percentage inhibition of the number of cough in an individual with interstitial lung disease.

In one embodiment treatment of cough associated with interstitial lung disease means that the severity of cough is reduced. This may be evaluated using a cough severity score.

In one embodiment severity of cough is defined as follows (cough severity score 0-4): 0 no cough at all; 1 occasional hems; 2 mild, isolated cough, without additional symptoms; 3 moderate, paroxysmal cough, without additional symptoms; 4 severe, strenuous cough, accompanied by chest discomfort.

In one embodiment the cough severity score is reduced by approximately 1 point, such as by 2 points, such as by 3 points, such as by 4 points.

In one embodiment the cough severity score (0-10) is reduced by 0 to 0.5 point, such as 0.5 to 1 points, such as by 1 to 1.5 points, such as by 1.5 to 2 points, such as by 1.5 to 2 points, such as by 1.5 to 2 points, such as by 2 to 2.5 points, such as by 2.5 to 3 points, such as by 3 to 3.5 points, such as by 3.5 to 4 points.

In one embodiment cough severity is reduced to approximately 90%, such as 80%, such as 70%, such as 60%, such as 50%, such as 40%, such as 30%, such as 20%, such as 10% of the observed cough severity without treatment or prior to treatment.

A combined cough frequency/severity scoring may be suitable for clinical practice and can improve the identification of dynamic cough modifications during treatment period as compared with the conventional frequency score method.

In one embodiment treatment of cough associated with interstitial lung disease means that coughing is acutely reduced. In one embodiment treatment of cough associated with interstitial lung disease means that coughing is chronically reduced.

Combination Therapies

The compounds or compositions of the present invention may be combined with or comprise one or more additional active ingredients which are understood as other therapeutically effective compounds or pharmaceutically acceptable derivatives thereof.

In one embodiment the composition comprising a compound of formula (I) (suplatast tosilate), or a pharmaceutically acceptable derivative thereof, comprises, separately or together, one or more additional active pharmaceutical ingredients.

In one embodiment the composition comprising a compound of formula (I) (suplatast tosilate), or a pharmaceutically acceptable derivative thereof, comprises, separately or together, one or more additional active pharmaceutical ingredients used for the treatment of cough.

In one embodiment said one or more additional active pharmaceutical ingredients comprise ingredients used for the treatment of cough (anti-tussives).

Anti-tussives encompassed herewith include Expectorants (help thin mucus, making it easier to cough up, e.g. comprising guaifenesin), Suppressants (help cut the number of times you cough, often comprising dextromethorphan, other cough suppressants include camphor, eucalyptus oil, and menthol) and combination cough products having more than one active ingredient (e.g. comprising for example both guaifenesin and dextromethorphan). Cough medicines may also contain ingredients to help coat and soothe the throat. Combination products may have medicines to ease other symptoms that may include decongestants for stuffy nose, antihistamines for allergies or a runny nose, or painkillers.

In one embodiment said one or more additional active pharmaceutical ingredients used for the treatment of cough (anti-tussives) is selected from the group consisting of codein, aspirin, dextromethorphan, guaifenesin, camphor, eucalyptus oil, menthol, opium, benzonatate, pentoxyverine, diphenhydramine, oxymetazoline, levodropropizine, noscapine, theobromine, benzonatate, triprolidine, pseudoephedrine, chlorpheniramine, chlorpheniramine, hydrocodone, pseudoephedrine, hydrocodone and chlorpheniramine, colistimethate injection, homatropine, different anti-histamines and proton pump inhibitors and potential new types of compounds (e.g. modulators of P2X3, TRPV1, TRPA1, CB-2 and NK-1 receptors).

In another embodiment said one or more additional active pharmaceutical ingredients comprise ingredients used for the treatment of the underlying cause of the cough. This includes causes associated with cough associated with interstitial lung disease including idiopathic pulmonary fibrosis (IPF)), chronic obstructive pulmonary disease (COPD), congestive heart disease and sarcoidosis. Such treatments include Ofev (nintedanib), pirfenidone, nintedanib, PRM-151, omipalisib, TD139 and other inhibitors of galectin-3, MLN0128 and other inhibitors of mTOR, BMS-986020, FG-3019, lebrikizumab, SAR156597 and other antibodies against interleukin-13, simtuzumab, STX-100 and tralokinumab.

In one embodiment the combination of additional medicaments has a dose-sparing effect of lowering the required dosage of the medication used in combination with the compound of the present invention.

In one embodiment of the present invention, the composition comprising a compound of formula (I) as defined herein, and the additional active ingredient, are administered simultaneously, sequentially or separately.

In one embodiment of the present invention, the composition comprising a compound of formula (I) as defined herein is administered before the additional active ingredient. In another embodiment, the composition comprising a compound of formula (I) as defined herein is administered simultaneously with the additional active ingredient. In yet another embodiment, the composition comprising a compound of formula (I) as defined herein is administered after the additional active ingredient.

Routes of Administration

It will be appreciated that the preferred route of administration will depend on the general condition and age of the subject to be treated, the nature of the condition to be treated, the location of the tissue to be treated in the body and the active ingredient chosen.

In one embodiment of the present invention, the composition comprising a compound of formula (I) as defined herein is administered by systemic administration, local administration, enteral administration or parenteral administration. Appropriate dosage forms for such administration may be prepared by conventional techniques.

Systemic Administration

Systemic administration is capable of introducing the agent into the blood stream to ultimately target the sites of desired action.

Such routes of administration are any suitable routes, such as an enteral route, the oral, rectal, nasal, pulmonary, buccal, sublingual, transdermal, intracisternal, intraperitoneal, and parenteral (including subcutaneous, intramuscular, intrathecal, intravenous and intradermal) route.

In one embodiment, the composition comprising a compound of formula (I) as defined herein is administered by systemic administration.

Oral Administration

Oral administration is normally for enteral drug delivery, wherein the agent is delivered through the enteral mucosa. Syrups and solid oral dosage forms, such as tablets, capsules and the like, are commonly used.

In one embodiment, the composition comprising a compound of formula (I) as defined herein is administered by oral administration.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration. Furthermore, parenteral administration includes inhalations and topical administration.

Accordingly, the agent may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent may be administered topically to cross the skin.

The subcutaneous and intramuscular forms of parenteral administration are generally preferred.

In one embodiment, the composition comprising a compound of formula (I) as defined herein is administered by pulmonal, bronchial or intratracheal administration by inhalation or installation. Delivery to the pulmonal space in one embodiment includes use of aerosolizers or nebulizers.

Local Treatment

The agent according to the invention may be used as a local treatment, i.e. be introduced directly to the site(s) of action. Accordingly, the agent may be applied to the skin or mucosa directly, or the agent may be injected into the site of action, for example into the diseased tissue or to an end artery leading directly to the diseased tissue.

Dosage According to the present invention, the composition comprising a compound of formula (I) is administered to individuals in need of treatment in pharmaceutically effective doses. A therapeutically effective amount of a compound is an amount sufficient to cure, prevent, reduce the risk of, alleviate or partially arrest the clinical manifestations of a given disease and its complications. The amount that is effective for a particular therapeutic purpose will depend on the severity and the sort of the disorder as well as on the weight and general state of the subject. The compounds may be administered one or several times per day, such as from 1 to 8 times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day. Alternatively, the compounds may be administered less than once a day, for example once a day, such as once every second day, for example once every third day, such as once every fourth day, for example once every fifth day, such as once every sixth day, for example once every week.

In one embodiment the composition comprising a compound of formula (I) as defined herein is administered in a therapeutically effective amount, such as in an amount of 1 mg to 1000 mg compound of formula (I) (calculated as the free base) per day.

It follows that in one embodiment the compound is administered in an amount of 1 mg to 10 mg, such as 10 to 20 mg, 20 to 40 mg, 40 to 60 mg, 60 to 80 mg, 80 to 100 mg, 100 to 150 mg, 150 to 200 mg, 200 to 250 mg, 250 to 300 mg, 300 to 350 mg, 350 to 400 mg, 400 to 500 mg, 500 to 600 mg, 600 to 700 mg, 700 to 800 mg, 800 to 900 mg, 900 to 1000 mg, 1000 to 1250 mg, 1250 to 1500 mg, 1500 to 1750 mg, 1750 to 2000 mg, 2000 to 2250 md, 2250 to 2500 mg, 2500 to 2750 mg, 2750 to 3000 mg, 3000 to 3500 mg, 3500 to 4000 mg, for example 4000 to 5000 mg per day.

Per day means the dosage may be given in one dosage or divided in multiple dosages per day, including once a day (QD), twice a day (BID) and/or three times a day (TID).

In one embodiment the compound is administered 100 mg TID, such as 500 mg TID, such as 800 mg TID, such as 1000 mg TID. In one embodiment the compound is administered 100-250 mg TID, such as 250-500 mg TID, such as 500-800 mg TID, such as 800-1000 mg TID.

In one embodiment the compound is administered 200 mg BID, such as 500 mg BID, such as 800 mg BID, such as 1000 mg BID. In one embodiment the compound is administered 200-500 mg BID, such as 500-800 mg BID, such as 800-1000 mg BID, such as 1000-1500 mg BID.

In another embodiment the compound is administered in an amount of 0.01 mg/kg bodyweight to 40 mg/kg bodyweight, such as 0.01 mg/kg bodyweight to 0.05 mg/kg bodyweight, 0.05 to 0.1 mg/kg bodyweight, 0.1 to 0.5 mg/kg bodyweight, 0.5 mg to 1 mg/kg bodyweight, 1 to 2 mg/kg bodyweight, 2 to 3 mg/kg bodyweight, 3 to 5 mg/kg bodyweight, 5 to 10 mg/kg bodyweight, 10 to 15 mg/kg bodyweight, 15 to 20 mg/kg bodyweight, 20 to 30 mg/kg bodyweight, for example 30 to 40 mg/kg bodyweight.

Formulation

In one embodiment the composition comprising a compound of formula (I) as defined herein is a pharmaceutical composition, such as a pharmaceutically safe composition. The composition comprising a compound of formula (I) as defined herein may be administered in any suitable way e.g. orally, sublingually, or parenterally, and it may be presented in any suitable form for such administration, e.g. in the form of solutions, suspension, aerosols, tablets, capsules, powders, syrups, implant or dispersions for injection.

In one embodiment, the composition comprising a compound of formula (I) as defined herein is formulated for pulmonary inhalation.

In one embodiment, the composition comprising a compound of formula (I) as defined herein is formulated as an aerosol. An aerosol is a colloid of fine solid particles or liquid droplets, in air or another gas.

In one embodiment, the composition comprising a compound of formula (I) as defined herein is formulated as a suspension.

In one embodiment, the composition comprising a compound of formula (I) as defined herein is formulated as an oral dose form, such as a solid oral dose form or pharmaceutical entity, such as tablets or capsules, or a liquid oral dose form. Methods for the preparation of solid pharmaceutical preparations are well known in the art.

In another embodiment the composition comprising a compound of formula (I) as defined herein is formulated as an injectable dose form.

In one embodiment the composition comprising a compound of formula (I) as defined herein is formulated in the form of a solid pharmaceutical entity, suitably as a tablet or a capsule The compound (I) as the free base or the salt thereof may be administered alone or in combination with pharmaceutically acceptable carriers or excipients, in either single or multiple doses. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

EXAMPLES

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

Example 1: Evaluation of Suplatast Tosilate in Cough Induced by Enalapril Plus Citric Acid in Guinea Pigs The method is described in detail by Zhou et al: Pharmacology. 2015; 95(1-2): 36-41. In brief: Male guinea pigs 300-350 g bodyweight (Harlan MD, distributed by INNOVO Ltd., Hungary) were used. The animals were housed in open cages in a temperature-controlled and ventilated environment (21-23° C.) with a 12-hour light-dark cycle. Water and standard ascorbic acid containing guinea pig chow were provided ad libitum. The protocol has been approved by the Hungarian Food Chain Safety and Animal Health Directorate (PEI/001/3083-6/2014) and was carried out in accordance with European Directive 86/609/EEC.

The enalapril maleate was dissolved in sterile saline (Salsol infusion, Teva) at 1.3 mg/mL concentration and was applied subcutaneously at 1.3 mg/kg dose (1 mL/kg b.d.w. volume from the 1.3 mg/mL solution) 30 min before vehicle, suplatast tosilate or administration.

The vehicle for suplatast tosilate was 10% PEG400/saline mixture. Suplatast tosilate was well soluble in this mixture. ST was administered intraperitoneally at 30 mg/kg dose (1 ml/kg b.d.w. volume from the 30 mg/mL solution/suspension) 30 min before citric acid challenge. 6 guinea pigs were included in the vehicle group and in the ST group.

The guinea pigs were exposed to 10% citric acid spray 30 min after the test item administration. The 10% citric acid spray was generated by a compressed air nebulizer (DeVilbiss Pulmoaid) connected to a transparent chamber (6.7 l volume). Compressed air with a flow of 0.16 l/s and pressure of 0.5 bar produced the spray. The citric acid vapour penetrated into the chamber through a short tube driven by constant air flow. The animals were put into a transparent chamber individually and exposed to the citric acid (10 w/v % citric acid dissolved in distilled water) aerosol for 3 minutes. The number of coughs during the 3 min inhalation period and the subsequent 5 min was counted. The coughing of the animals was defined as a strong contraction of abdomen which was followed by forced expiration through the opened mouth of the animals. The sound of the cough was monitored by a microphone connected to a loudspeaker placed into the cough chamber. A trained technician monitored the exposed animals and counted the cough numbers.

The average cough numbers in each group was expressed as mean±S.E.M. The percentage antitussive effect was also calculated.

$$\text{Percentage antitussive effect} = 100 - \left[\frac{\text{Cough number in the treated group}}{\text{Cough number in the control group}} \times 100\right]$$

The animals in the vehicle group produced 11.2±2.6 coughs during the whole 8-min observational period.

The cough number in the suplatast tosilate treated group was lower (7.2±2.8) than that of vehicle group (11.2±2.6) indicating the antitussive effect of suplatast tosilate.

Example 2: Evaluation of Suplatast Tosilate in Model of Reduction of Cough in Pre-Clinical Model of Pulmonary Fibrosis The model of bleomycin-induced cough exacerbations has been described in detail by J. A. Fernandez-Blanco et al: Clinical Science (2015) 129, 1001-1010).

Animals

Male Dunkin-Hartley guinea pigs (300-350 g) are purchased from a commercial breeder. Animals are housed in groups of three or four in a room with controlled temperature (20-24° C.), humidity (45-65%), air cycles (10-20 renovations/h) and a 12 h light/12 h dark cycle. Standard maintenance diet supplemented with vitamin C, irradiated hay and water is available ad libitum. Care and use of animals is undertaken in compliance with the European Community Directive 86/609/CEE for the use of laboratory animals.

Bleomycin-Induced Model of Pulmonary Fibrosis

Animals under 2% isoflurane anaesthesia receive a single dose of 8 μl/kg bleomycin sulfate (B2434; Sigma-Aldrich) or vehicle (0.2 ml saline) by intratracheal administration using MicroSprayer® Aerosolizers (Model IA-1B-GP for Guinea Pig; PennCentury). Bleomycin is prepared immediately before administration. At the end of the study, animals are killed by intraperitoneal administration of sodium pentobarbital (200 mg/kg; Dolethal; Vetoquinol).

Cough Induction

At days 14 and 21 after bleomycin administration, cough reflex is evaluated in conscious unrestrained guinea pigs using whole-body plethysmography chambers (Buxco Research Systems. Citric acid (Sigma-Aldrich) is dissolved and diluted in 0.9% saline. After a 2 min baseline reading of airway function, animals are exposed to one of the challenges. Citric acid (0.3 M) is administered by aerosol with a micropump nebulizer (Aeroneb Lab; Aerogen) whereas AITC (10 mM) is delivered via an ultrasonic nebulizer (De Vilbiss). The number of coughs is counted during the exposure to citric acid (10 min). Coughs are assessed and counted by a trained observer in agreement with the ERS guidelines on the assessment of cough (Morice et al. (2007) Eur. Respir. J. 29, 1256-1276) considering changes in posture (quick large abdominal movement and opening of the mouth), characteristic sounds and changes in airflow, recorded with the Finepointe software (Buxco Research Systems).

Drug Treatment

The vehicle for suplatast tosilate (ST) is 10% PEG400/saline mixture. ST is well soluble in this mixture. ST is administered intraperitoneally at 30 mg/kg dose (1 ml/kg b.d.w. volume from the 30 mg/mL solution/suspension) 30 min before citric acid challenge. 6 guinea pigs were included in the vehicle and in the ST groups.

Data Analysis

Time-course data are shown as means+/−S.E.M. Comparisons between multiple groups were performed using two-way ANOVA followed by Sidak's tests. Cough counts are expressed as the median+/−interquartile range. In this case, comparisons between groups are performed using non-parametric Mann-Whitney tests. The percentages of enhancement in response to tussive agents are calculated in respect to the median of the corresponding saline group.

Example 3: Evaluation of Suplatast Tosilate in Model of Reduction of Cough in Pre-Clinical Model of Pulmonary Fibrosis The study is conducted as described in example 2 with the following exceptions:

Drug Treatment:

Starting from 7 days after exposure to bleomycin the animals (n=8) is treated with ST (30 mg/kg, ip) once daily until day 14. On day 14 ST is administered 30 minutes before cough is induced with capsaicin (30 M) prepared by taking a 1 mM stock solution of capsaicin (Sigma-Aldrich) in 100% ethanol and further dissolved with saline to obtain a 30 μM concentration.

Example 4: Evaluation of Suplatast Tosilate in Model of Reduction of Cough in Pre-Clinical Model of Pulmonary Fibrosis The study was conducted as described in example 2, with the following exceptions. The bleomycin-induced cough modes is described J. A. Fernandez-Blanco et al: Clinical Science (2015) 129, 1001-1010).

The objective of the present study was to evaluate the potential anti-tussive effect of suplatast tosilate on capsaicin inhalation-induced cough on naïve and bleomycin-treated guinea pigs.

Experimental Set-Up

Male guinea pigs 300-350 g bodyweight (Harlan MD, distributed by INNOVO Ltd., Hungary) were used. The animals were housed in individually ventilated cabinets in a temperature-controlled and ventilated environment (21-23° C.) with a 12-hour light-dark cycle. Water and standard ascorbic acid containing guinea pig chow were provided ad libitum. The protocol has been approved by the Hungarian Food Chain Safety and Animal Health Directorate (PEI/001/3083-6/2014) and was carried out in accordance with European Directive 86/609/EEC.

Suplatast tosilate (racemate) and reference compound codeine were dissolved in saline (0.5% NaCl) at 15 mg/mL concentration. Suplatast tosilate was administered intraperitoneally at 30 mg/kg dose (2 ml/kg b.d.w. volume from the 15 mg/kg solution) 30 min before capsaicin challenge. Codeine is a known cough suppressant.

Three experimental groups were involved in this study: Vehicle, suplatast tosilate and codeine treated groups. Each group contained n=16 guinea pigs. Altogether, 48 guinea pigs were used for this study.

On day 0 the naïve animals were treated i.p. either with codeine or suplatast tosilate. 30 min later the cough challenge was applied. 14 days later the animals were anaesthetized by ketamin/xilazine/acepromazine 10/2/0.1 mg/kg at 1 mL/kg i.m. The trachea was prepared and 8 U/kg bodyweight (1 mL/kg volume in sterile saline) bleomycin was injected slowly into the trachea. The wound was closed by sutures. 14 days after bleomycin injection the animals were treated with the test molecules and exposed to capsaicin spray again.

The capsaicin cough-challenge protocol was applied both on day 0 naïve animals and on day 28 on bleomycin treated animals. The guinea pigs were exposed to 30 μM capsaicin spray 30 min after the test item administration. The 30 μM capsaicin spray was generated by a compressed air nebulizer (DeVilbiss Pulmoaid) connected to a transparent chamber (6.7 l volume). Compressed air with a flow of 0.16 l/s and pressure of 0.5 bar produced the spray. The capsaicin vapour penetrated into the chamber through a short tube driven by constant air flow. The animals were put into a transparent chamber individually and exposed to the capsaicin (30 μM capsaicin was diluted by water from 10-2 M alcoholic capsaicin stock solution) aerosol for 10 minutes. The number of coughs during the 10 min inhalation period and the subsequent 5 min was counted. The coughing of the animals was defined as a strong contraction of abdomen which was followed by forced expiration through the opened mouth of the animals. Two trained technicians monitored in parallel the exposed animals and counted the cough numbers independently from each-others.

The cough numbers in each group were expressed as median and inter quartile range on the figures and mean±SD on tables. The percentage antitussive effect was also calculated.

Percentage antitussive effect =

$$100 - \left[\frac{\text{Cough number in the treated group}}{\text{Cough number in the control group}} \times 100\right]$$

Results

Naïve Animals

The animals in the vehicle group produced 9.3±4.6 coughs in the exposure period and 2.4±6.4 in the 5 min post-exposure period. Altogether, during the whole 15-min observation period the cough number was 11.7±9.3 in the vehicle group. Codeine as reference compound showed 43.9% p<0.01 antitussive effect based on the counted cough numbers in the 10 min exposure period, and almost abolished (97.4% p<0.05) the cough reaction in the post exposure period. Altogether, the percentage antitussive effect of codeine was 55.0% p<0.001 during the whole 15-min observation period. In contrast, suplatast tosilate did not show antitussive effect in the exposure and post-exposure observation periods.

TABLE 1

The cough number and the percentage antitussive effect on 30 uM capsaicin cough challenge is summarised on naive animals.
Mean ± SD; n = 16; ANOVA followed by Kruskal Wallis test.

Naïve animals

| | Capsaicin | | | | | |
|---|---|---|---|---|---|---|
| | 10 min exposure | | 5 min observation | | 10 + 5 min | |
| Groups | mean cough | SD | mean cough | SD | mean cough | SD |
| vehicle i.p. | 9.3 | 4.6 | 2.4 | 6.4 | 11.7 | 9.3 |
| Codeine 30 mg/kg i.p. | 5.2 | 3.5 | 0.1 | 0.2 | 5.3 | 2.9 |
| Percentage inhibition | 43.9 | p < 0.01 | 97.4 | p < 0.05 | 55 | p < 0.001 |
| Suplatast 30 mg/kg i.p. | 9.8 | 4.9 | 3.7 | 7.2 | 13.4 | 11.8 |
| Percentage inhibition | −5.4 | n.s. | −51.9 | n.s. | −15 | n.s. |

Bleomycin-Treated Animals

The animals in the vehicle group produced 52.9±26.2 coughs in the exposure period and 22.4±13.2 in the 5 min post-exposure period. Altogether, during the whole 15-min observational period the cough number was 75.3±32.7 in the vehicle group. Codeine showed 72.9% p<0.001 antitussive effect based on the counted cough numbers in the 10 min exposure period and 76.2% p<0.001 antitussive effect in the 5-min post exposure period, with a combined antitussive effect of codeine of 73.9% p<0.001 during the whole 15 minutes observation period. Suplatast tosilate showed 42.8% p<0.01 antitussive effect in the exposure and 77.7% p<0.001 in the post-exposure observation period; altogether, the antitussive effect of suplatast was 53.2% p<0.01 during the whole 15-min observation period.

TABLE 2

The cough number and the percentage antitussive effect on 30 uM capsaicin cough challenge is summarised on Bleomycin treated animals.
Mean ± SD; n = 14-16; ANOVA followed by Kruskal Wallis test.

| | Bleomycin-treated | | | | | |
|---|---|---|---|---|---|---|
| | Capsaicin | | | | | |
| | 10 min exposure | | 5 min observation | | 10 + 5 min | |
| Groups | mean cough | SD | mean cough | SD | mean cough | SD |
| vehicle i.p. | 52.9 | 26.2 | 22.4 | 13.2 | 75.3 | 32.7 |
| Codeine 30 mg/kg i.p. | 14.3 | 10.3 | 5.3 | 8.6 | 19.7 | 17.2 |
| Percentage inhibition | 72.9 | P < 0.001 | 76.2 | P < 0.001 | 73.9 | P < 0.001 |
| Suplatast 30 mg/kg i.p. | 30.3 | 27.9 | 5 | 8.4 | 35.3 | 23.4 |
| Percentage inhibition | 42.8 | P < 0.01 | 77.7 | P < 0.001 | 53.2 | P < 0.01 |

To conclude, capsaicine evoked relevant cough responses in guinea pigs during the exposure and post-exposure observation periods on naïve animals. The capsaicin-induced cough response increased 14 days after bleomycin treatment in the vehicle group.

Codeine showed antitussive effect both on naïve and bleomycin-treated animals. Suplatast tosilate did not show antitussive effect on naïve animals. However, suplatast tosilate showed relevant and statistically significant antitussive effect on bleomycin treated animals.

Example 5: Evaluation of Suplatast Tosilate in Patients Suffering from Idiopathic Pulmonary Fibrosis A randomized, double-blind, placebo-controlled, crossover study will measure the effect of ST compared to placebo at a dose of 100 mg three times per day for two weeks on cough frequency, as measured objectively by a cough recording device. Following a two-week washout period, patients are then crossed over to the alternate treatment arm and dosed twice daily for an additional two weeks. Cough frequency is measured at each baseline and at the end of each treatment period.

REFERENCES

Fernández-Blanco J A et al: Clin Sci (Lond). 2015, 129(12): 1001-10.
Ishiura et al: Arzneimittel-Forschung (Drug Research) 2008; 58(6):297-302.
Methling et al: Drug Metabolism and Disposition (2009), 37:479-493.
Miyamoto et al: Gen Thorac Cardiovasc Surg. 2009; 57(9): 463-6.
Morice, A. H et al. (2007). Eur. Respir. J. 29, 1256-1276.
Myou et al: Clinical and Experimental Allergy, 2001, 31, 1939-1944.
Shioya et al: Eur J Clin Pharmacol (2002) 58: 171-176.
Suzuki et al. Drug Metab. Dispos. (1999), 27: 1254-1259.
Tada et al: J. Med. Chem. 1998, 41, 3330-3336.
Zhou et al: Pharmacology. 2015; 95(1-2): 36-41.

The invention claimed is:

1. A method of alleviating cough in a patient diagnosed with an interstitial lung disease, said method comprising one or more steps of administering a composition comprising a compound of formula (I):

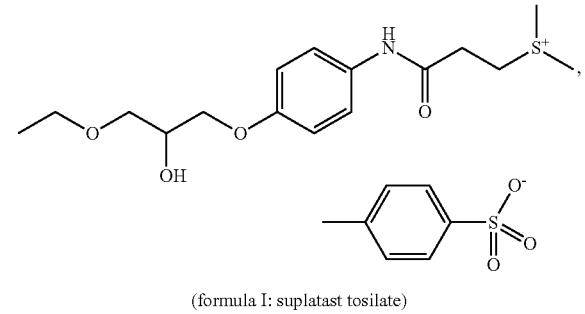

(formula I: suplatast tosilate)

or a pharmaceutically acceptable salts, esters and crystal forms thereof, to an individual in need thereof, wherein the individual has a cough caused by an interstitial lung disease.

2. The method according to claim 1 wherein said suplatast tosilate is selected from the group consisting of:
   i) the racemic compound,
   ii) the (+)-suplatast tosilate enantiomer, and
   iii) the (−)-suplatast tosilate enantiomer.

3. The method according to claim 1, wherein said cough is a chronic cough.

4. The method according to claim 1, wherein said cough is a symptom of lung fibrosis (pulmonary fibrosis).

5. The method according to claim 1, wherein said interstitial lung disease is selected from the group consisting of:
   idiopathic pulmonary fibrosis (IPF),
   honeycomb lung caused by ILD, such as IPF,
   chronic obstructive pulmonary disease (COPD),
   sarcoidosis,
   congestive heart disease,
   pulmonary veno-occlusive disease,
   pulmonary edema,
   chronic eosinophilic pneumonia,
   cryptogenic organizing pneumonia,
   pulmonary alveolar proteinosis, connective tissue associated interstitial lung diseases,
pulmonary fibrosis associated with connective tissue diseases,
chronic aspiration,
drug-induced lung disease,
inhaled substance-induced lung disease, such as mineral dusts,
pneumoconiosis,
infection-induced lung disease,
malignancy-induced lung disease,
silicosis,
berylliosis,
asbestosis,
hard metal lung disease,
mixed dust pneumoconiosis,
graphitosis,
talcosis,
coal workers pneumoconiosis,
carmustine related pulmonary fibrosis,
respiratory bronchiolitis,
alveolar microlithiasis
pulmonary langerhans cell histiocytosis,
ground glass opacities,
respiratory bronchiolitis associated interstitial lung disease,
nonspecific interstitial pneumonia,
desquamative interstitial pneumonia,
usual interstitial pneumonia,
lymphoproliferative disorders,
lymphoma,
pulmonary lymphangioleiomyomatosis,
lymphangitic carcinomatosis,
lymphadenopathy,
lymphocytic interstitial pneumonia, and
combined pulmonary fibrosis and emphysema.

6. The method according to claim 4, wherein said cough is caused by idiopathic pulmonary fibrosis (IPF).

7. The method according to claim 1, wherein said administration reduces cough symptom in an individual with interstitial lung disease.

8. The method according to claim 7, wherein said administration reduces the frequency of cough.

9. The method according to claim 8, wherein said administration reduces the frequency of cough evaluated by the cough frequency score (0-10; 0=I never cough; 10=I cough all day), wherein the cough frequency score (0-10) is reduced by 0 to 1 points, 1 to 2 points, such as by 2 to 3 points, such as by 3 to 4 points, such as by 4 to 5 points, such as by 5 to 6 points, such as by 6 to 7 points, such as by 7 to 8 points, such as by 8 to 9 points, such as by 9 to 10 points.

10. The method according to claim 8, wherein said administration reduces the frequency of cough to approximately 10 to 20%, such as 20 to 30%, such as 30 to 40%, such as 40 to 50%, such as 50 to 60%, such as 60 to 70%, such as 70 to 80%, such as 80 to 90% of the observed frequency without treatment or prior to treatment.

11. The method according to claim 10, wherein said administration reduces cough to 20 to 100%, such as 30 to 90%, such as 40 to 80%, such as 40% or 50% or more percentage inhibition of the number of cough in an individual with interstitial lung disease.

12. The method according to claim 10, wherein said administration reduces the severity of cough.

13. The method according to claim 12, wherein said administration reduces the severity of cough evaluated by the cough severity score (0-4), wherein the cough severity score is reduced by 0 to 0.5 point, such as 0.5 to 1 points, such as by 1 to 1.5 points, such as by 1.5 to 2 points, such as by 1.5 to 2 points, such as by 1.5 to 2 points, such as by 2 to 2.5 points, such as by 2.5 to 3 points, such as by 3 to 3.5 points, such as by 3.5 to 4 points.

14. The method according to claim 1, wherein said composition comprises, separately or together, one or more additional active pharmaceutical ingredients.

15. The method according to claim 1, wherein said composition comprises, separately or together, one or more additional active pharmaceutical ingredients used for the treatment of cough.

16. The method according to claim 1, wherein said composition is administered by administration selected from the group consisting of systemic administration, oral administration, or by pulmonal, bronchial or intratracheal administration.

17. The method according to claim 1, wherein said compound is administered in an amount of 1 mg to 10 mg per day, 10 to 20 mg, 20 to 40 mg, 40 to 60 mg, 60 to 80 mg, 80 to 100 mg, 100 to 150 mg, 150 to 200 mg, 200 to 250 mg, 250 to 300 mg, 300 to 350 mg, 350 to 400 mg, 400 to 500 mg, 500 to 600 mg, 600 to 700 mg, 700 to 800 mg, 800 to 900 mg, 900 to 1000 mg, 1000 to 1250 mg, 1250 to 1500 mg, 1500 to 1750 mg, 1750 to 2000 mg, 2000 to 2250 md, 2250 to 2500 mg, 2500 to 2750 mg, 2750 to 3000 mg, 3000 to 3500 mg, 3500 to 4000 mg, 4000 to 5000 mg per day.

18. The method according to claim 1, wherein said compound is administered once a day (QD), twice a day (BID) or three times a day (TID).

19. The method according to claim 1, wherein said composition is pharmaceutically safe.

20. The method according to claim 16, wherein said composition is administered by pulmonal, bronchial or intratracheal administration by inhalation or installation.

21. The method of claim 1, further comprising selecting the individual based on the presence of the cough and the interstitial lung disease.

* * * * *